United States Patent [19]

Kamber et al.

[11] 4,316,890
[45] Feb. 23, 1982

[54] PEPTIDES AND PROCESSES FOR THE MANUFACTURE THEREOF

[75] Inventors: Bruno Kamber, Arlesheim; Hans Rink, Riehen; Peter Sieber, Reinach, all of Switzerland

[73] Assignee: Ciba-Geigy Corporation, Ardsley, N.Y.

[21] Appl. No.: 129,066

[22] Filed: Mar. 10, 1980

[30] Foreign Application Priority Data

Mar. 16, 1979 [CH] Switzerland .................. 2506/79

[51] Int. Cl.³ .................. A61K 37/00; C07C 103/52
[52] U.S. Cl. .................. 424/177; 260/112.5 S
[58] Field of Search .................. 260/112.5 S; 424/177

[56] References Cited

U.S. PATENT DOCUMENTS

| | | | |
|---|---|---|---|
| 4,020,157 | 4/1977 | Abraham et al. | 260/112.5 S |
| 4,098,782 | 7/1978 | Sarantakis | 260/112.5 S |
| 4,115,554 | 9/1978 | Veber | 260/112.5 S |

FOREIGN PATENT DOCUMENTS 2019411  3/1979  United Kingdom ......... 260/112.5 S

OTHER PUBLICATIONS

J. Rivier, et al., "Peptides", (1976) 427–451.

*Primary Examiner*—Delbert R. Phillips
*Attorney, Agent, or Firm*—Prabodh I. Almaula

[57] ABSTRACT

The somatostatin-analogous peptides according to the invention of the general formula

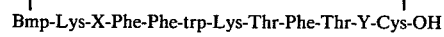

Bmp-Lys-X-Phe-Phe-trp-Lys-Thr-Phe-Thr-Y-Cys-OH 3   4  5  6   7 8   9   10  11  12 13  14 in which
  Bmp represents the desaminocysteine radical
  X represents Asn or His,
  trp represents D-Trp that may be substituted in the benzene ring by a halogen atom, and
  Y represents the radical of a secondary α-amino acid having a maximum of 8 carbon atoms and the corresponding peptide amides and also acid addition salts and complexes thereof are distinguished by strong insulin-antagonistic and glucagon-antagonistic effects and are therefore therapeutically acceptable, preferably in the form of pharmaceutical preparations, in similar indications to those of somatostatin, especially also as antidiabetics. The compounds are manufactured by conventional processes of peptide synthesis, especially by liberation from corresponding protected intermediates and by the formation of the cystine disulphide bridge by means of oxidation.

10 Claims, No Drawings

PEPTIDES AND PROCESSES FOR THE MANUFACTURE THEREOF

The invention relates to new peptides of the somatostatin type and processes for the manufacture thereof, pharmaceutical preparations containing these compounds and the use of these compounds or preparations for therapeutic purposes. The invention relates especially to peptides that have, in comparison with somatostatin, an amino acid sequence that is shorter by the first 2 N-terminal amino acids and is modified by some replacement members.

The peptides according to the invention which are analogous to somatostatin include modified Des-[Ala$^1$-Gly$^2$]-desamino-Cys$^3$-somatostatins of the general formula

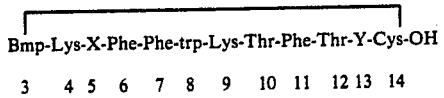

Bmp-Lys-X-Phe-Phe-trp-Lys-Thr-Phe-Thr-Y-Cys-OH 3  4 5  6  7  8  9  10 11 12 13 14 in which
Bmp represents the desaminocysteine radical (i.e. the β-mercaptopropionyl radical),
X represents Asn or His,
trp represents D-Trp that may be substituted in the benzene ring by a halogen atom, and
Y represents the radical of a secondary α-amino acid having a maximum of 8 carbon atoms
and the corresponding peptide amides and also acid addition salts and complexes of all these compounds.

The halogen atom optionally present in the benzene ring of the D-tryptophane$^8$ radical is especially a chlorine or fluorine atom that is preferably in the 5-position; special mention should be made of the 5-fluoro-D-tryptophyl$^8$ radical.

The secondary α-amino acid designated Y is an α-lower alkylamino-lower alkylcarboxylic acid in which the two lower alkyl radicals may be connected to one another by a C-C bond, an oxygen atom, a sulphur(II) atom or an optionally lower alkylated nitrogen atom, each individual lower alkyl radical containing a maximum of 6 carbon atoms and both together containing a maximum of 7 carbon atoms. The lower alkyl radical forming the basis of the carbon skeleton of the carboxylic acid preferably has more than one carbon atom and is especially one that occurs in natural amino acids, such as butyl, isobutyl, pentyl and especially ethyl and isopentyl. The lower alkyl radical that occurs as the substituent of the amino group or the nitrogen bridge is preferably methyl. The C-C bond that optionally connects the two lower alkyl radicals is preferably a single bond. The α-amino group is preferably in a steric configuration that corresponds to the natural amino acids, i.e. the L-amino acids.

Preferred radicals Y are especially radicals of secondary α-amino acids that are known as naturally occurring amino acids, such as, especially, L-proline of the formula

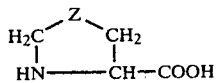

in which Z is a methylene group, or that are directly structurally analogous to these, such as, on the one hand, 4-oxaproline and especially 4-thiaproline of the above formula in which Z is oxygen or sulphur and, on the other hand, an N-lower alkylated, especially N-methylated, aliphatic amino acid, particularly N-methyl-L-leucine.

The preferred somatostatin analogues according to the invention are those compounds of the formula I in which
X represents Asn,
trp represents D-Trp or 5-fluoro-D-Trp and
Y represents Pro, Tpo (i.e. the radical of the above-characterised 4-thiaproline) or MeLeu (i.e. N-methyl-Leu).

Attention is drawn especially to: Desamino-Cys$^3$-D-Trp$^8$-Pro$^{13}$-somatostatin(3-14) [formula I; X=Asn, trp=D-Trp and Y=Pro]; Desamino-Cys$^3$-(5-F-D-Trp)$^8$-Pro$^{13}$-somatostatin(3-14) [formula I; X=Asn, trp=5-fluoro-D-Trp, Y=Pro]; Desamino-Cys$^3$-D-Trp$^8$-Tpo$^{13}$-somatostatin(3-14) [formula I; X=Asn, trp=D-Trp, Y=4-Thia-Pro] and Desamino-Cys$^3$-D-Trp$^8$-MeLeu$^{13}$-somatostatin(3-14) [formula I, X=Asn, trp=D-Trp, Y=N-Methyl-Leu]. All these preferred somatostatin analogues may also be in the form of acid addition salts or complexes.

Suitable acid addition salts are especially physiologically tolerable salts with conventional therapeutically acceptable acids; of the inorganic acids, hydrohalic acids, such as hydrochloric acid, but also sulphuric acid and phosphoric acid or pyrophosphoric acid, should be mentioned; of the organic acids, sulphonic acids, in particular, should be mentioned, such as benzenesulphonic acid or p-toluenesulphonic acid, or lower alkanesulphonic acids, such as methanesulphonic acid, also carboxylic acids, such as acetic acid, lactic acid, palmitic and stearic acid, malic acid, tartaric acids, ascorbic acid and citric acid.

Complexes should be understood as being the compounds the structures of which have not been fully clarified and which are formed when certain inorganic or organic substances are added to peptides and impart to these a prolonged action. Such substances are described, for example, for ACTH and other adrenocorticotropically active peptides. Examples are inorganic compounds that are derived from metals, such as calcium, magnesium, aluminium, cobalt and especially zinc, especially sparingly soluble salts, such as phosphates, pyrophosphates and polyphosphates, and hydroxides of these metals, also alkali metal polyphosphates, for example Calgon N®, Calgon 322® or Calgon 188®. Organic substances that bring about a prolongation of action are, for example, non-antigenic types of gelatin, for example polyoxygelatin, polyvinylpyrrolidone and carboxymethylcellulose, also sulphonic acid or phosphoric acid esters of alginic acid, dextran, polyphenols and polyalcohols, especially polyphloretin phosphate and phytic acid, as well as polymers and copolymers of basic or, especially, acidic amino acids, for example protamine or polyglutamic acid.

Unless otherwise indicated, the abbreviations of the amino acid residues refer to radicals of the α-amino acids of the L-series that occur naturally.

Unless otherwise indicated, the term "lower", wherever it occurs in connection with an organic radical or compound, indicates such a radical or compound having a maximum of 7 carbon atoms and preferably a maximum of 4 carbon atoms.

The new peptides according to the invention have a physiological action that is basically similar to the action of somatostatin. They can therefore be used advantageously in similar therapeutic indications to those of somatostatin, for example especially for the treatment of functional disorders in which the secretion of the somatotropic hormone or glucagon is abnormally high, such as in the case of acromegalia or diabetes. Since they also inhibit blood loss in the gastro-intestinal tract they can also be used successfully in this area of indication.

As is known, somatostatin, a cyclic tetradecapeptide of the formula

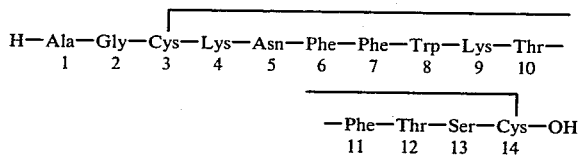

[Science 179,77 (1973)], inhibits the pituitary-controlled secretion of the somatotropic hormone (somatotropin). It also inhibits the secretory activity of the endocrine pancreas, such as the secretion of insulin and glucagon. In the case of somatostatin itself, these valuable properties cannot be used fully in practice since the inhibitory action is often desired only on one of the two glands while the other action should be suppressed if possible. In most cases, the inhibition of the pituitary secretion (i.e. that of the somatotropic hormone release) is in fact considered a disadvantage in the commonest therapeutic indications. For this reason, analogous structures were sought in the case of which a dissociation of the inhibitory effects can be achieved by suitable modification of the basic sequence, especially by the omission of individual original amino acids and/or the exchange thereof for other, often "unnatural", amino acids.

Surprisingly, it has now been found that it is possible to replace some of these original amino acids in a shortened molecule of somatostatin by other, even "unnatural", amino acids, which have no appreciable effect individually, in such a manner that a part of the physiological activity is not only maintained but even increased. Thus, in comparison with somatostatin, the compounds according to the invention exhibit increased inhibition of insulin and glucagon secretion while having the same or even a reduced inhibitory effect on the pituitary secretion of the somatotropic hormone.

The compounds according to the invention can be manufactured according to methods known per se. They are especially obtained by, in a compound of the general formula Bmp(C)-Lys(A)-X-Phe-Phe-trp-Lys(A')-Thr(B)-Phe-Thr(B')-Y-Cys-(C')-D     (II)

in which
X, trp and Y have the meanings given above and
A and A' each represents, independently of one another, an ε-amino-protecting group or hydrogen,
B and B' each represents, independently of one another, a hydroxyl-protecting group or hydrogen,
C and C' each represents, independently of one another, a mercapto-protecting group or hydrogen and
D represents a carboxyl-protecting group, the amino group NH₂ or hydroxyl, in any sequence, (a) splitting off any protecting groups present and (b) forming the disulphide bridge between the mercapto groups of both terminal acids optionally while simultaneously splitting off any mercapto-protecting groups present and, if desired, converting an end product formed as an acid addition salt into the corresponding free base or converting an end product formed as a base into an acid addition salt thereof and/or, if desired, isolating an end product in the form of a complex.

A variation of the process according to the invention consists in, for example, splitting off all protecting groups present in the starting material of the formula II defined above, with the exception of C or C', which operation can be carried out advantageously in a single step if suitable protecting groups are chosen, and then maintaining the intermediate compound of the formula II, in which A, A', B and B' each represents hydrogen, D represents hydroxyl or the amino group NH₂ and one of the symbols C and C' is hydrogen and the other is an n-alkylthio group or the radical

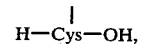

in a manner known per se, for example according to U.S. Pat. No. 3,929,758 or German Offenlegungsschrift No. 26 47 843, in a substantially oxygen-free solution at pH 5-10 for cyclisation. Particularly suitable protecting groups A, A', B and B' are, in this case, especially groups that can be split off by acidolysis, for example those given below; likewise, a group that can be split off by acidolysis, for example a benzyl group or a t-butylthio group, is preferred as one of the mercapto-protecting groups C and C' while the other is preferably an n-lower alkylthio group, such as a methylthio, ethylthio, propylthio or butylthio group.

A preferred variation of the processs according to the invention is that, in the starting material of the formula II, all protecting groups present are split off, which operation can be carried out advantageously in a single step if suitable protecting groups are chosen, and subsequently the intermediate compound of the formula II, in which A, A', B, B', C and C' each represents hydrogen and D represents hydroxyl or the amino group NH₂, is treated in a manner known per se with an oxidising agent, such as, especially, elementary iodine or oxygen.

An especially preferred variation of the process according to the invention is that a starting material of the formula II, in which X, trp, Y, A, A', B, B', C, C' and D have the meanings defined above, at least one of the symbols A, A', B, B' and D representing a protecting group, is oxidised, optionally while simultaneously splitting off any mercapto-protecting groups present, to form a cyclic disulphide intermediate of the formula

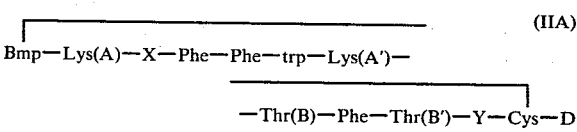

in which X, trp, Y and A, A', B, B' and D have the meanings given above, at least one of the symbols A, A', B, B' and D representing a protecting group, and the protecting group(s) present in this intermediate is (are) split off.

There may be used as ε-amino-protecting groups any of the amino-protecting groups usual in peptide chemistry, such as those described synoptically in the corresponding reference works, for example in Houben-Weyl: Methoden der organischen Chemie, 4th edition, volume 15/I; E. Wünsch (editor): Synthese von Peptiden. (Georg Thieme Verlag, Stuttgart; 1974).

Thus it is possible to use amino-protecting groups that can be split off, for example by reduction or by means of bases, for example especially the benzyloxycarbonyl group and benzyloxycarbonyl groups that are substituted in the aromatic moiety by halogen atoms, nitro groups, lower alkoxy groups and/or lower alkyl radicals, such as the p-chloro- and p-bromobenzyloxycarbonyl, p-nitrobenzyloxycarbonyl, p-methoxybenzyloxycarbonyl and p-tolyloxycarbonyl groups, or the isonicotinyloxycarbonyl group, also acyl groups, such as p-toluenesulphonyl, benzenesulphenyl, o-nitrobenzenesulphenyl and also formyl, trifluoroacetyl or phthaloyl.

An advantageous ε-amino-protecting group is an ethoxycarbonyl group that carries in the β-position a silyl group substituted by 3 hydrocarbon radicals, such as a triphenylsilyl, a dimethylbutylsilyl or especially a trimethylsilyl group. A β-(trihydrocarbylsilyl)-ethoxycarbonyl group of this type, such as a β-(trilower alkylsilyl)-ethoxycarbonyl group, for example especially the β-(trimethylsilyl)-ethoxycarbonyl group, forms together with the ε-amino group to be protected a corresponding β-trihydrocarbylsilylethoxycarbonylamino group (for example the β-trimethylsilylethoxycarbonylamino group) that is stable under the conditions of acidic hydrolysis and of hydrogenolysis but can be split off by the action of fluoride ions under quite specific, very mild conditions. In this respect it behaves analogously to the β-silylethyl ester group described below as a carboxyl-protecting group. (This similarity must be given particular consideration when synthesising; except for isolated cases, the use of one of these protecting groups excludes the simultaneous use of the other protecting group). Further details are given hereinafter in the description of the protection of the carboxyl group by a β-silylethyl ester.

Very particularly preferred are groups that can be split off by acidolysis, such as especially the tert.-butoxycarbonyl group and analogous groups, for example the tert.-amyloxycarbonyl, isopropoxycarbonyl, diisopropylmethoxycarbonyl, allyloxycarbonyl, cyclopentyloxycarbonyl, cyclohexyloxycarbonyl, d-isobornyloxycarbonyl and adamantyloxycarbonyl groups, and also groups of the aralkyl type, such as benzhydryl and triphenylmethyl (trityl), or certain aralkoxycarbonyl groups of the 2-(p-biphenylyl)-2-propoxycarbonyl type that are described in Swiss Patent Specification No. 509 266.

Suitable hydroxyl-protecting groups are any of the groups conventionally used in peptide chemisty for this purpose, cf. the work cited above (Houben-Weyl). Groups that can be split off by acidolysis, such as 2-tetrahydropyranyl and very especially tert.-butyl, are preferred. It is, however, also possible to use hydroxyl-protecting groups that can be split off by reduction or by means of bases, for example benzyl groups that may be substituted in the aromatic moiety by halogen, nitro and/or lower alkoxy, or lower alkanoyl radicals, such as acetyl, or aroyl radicals, such as benzoyl. If certain limiting measures are observed, it is also possible to proceed without protecting the hydroxyl groups.

As carboxyl-protecting groups it is possible to employ the groups normally used for this purpose, cf. the work cited above (Houben-Weyl). Thus, carboxyl groups are protected, for example, by the formation of hydrazides or by esterification. Suitable for esterification are, for example, lower optionally substituted alkanols, such as methanol, ethanol, cyanomethyl alcohol, 2,2,2-trichloroethanol, benzoylmethyl alcohol or especially tert.-butyl alcohol, or alternatively an optionally substituted benzyl alcohol. An especially advantageous category of substituted alkanols is ethyl alcohols that carry in the β-position a tri-substituted silyl group, such as a triphenylsilyl, dimethylbutylsilyl or especially a trimethylsilyl group. As described, for example, in Belgian Patent Specification No. 851,576, these alcohols are especially suitable for protecting the carboxyl groups because, although the corresponding β-silylethyl esters, for example β-(trimethylsilyl)-ethyl ester, have the stability of conventional alkyl esters, they can be split off selectively under mild conditions by the action of fluoride ions while retaining all the other protecting groups.

There may be used as mercapto-protecting groups any of the groups conventionally used for this purpose in peptide chemistry, the mercapto groups being protected especially by suitable acylation or alkylation. Suitable for acylation are, for example, the acetyl or benzoyl radical, a lower alkylcarbamoyl, for example ethylcarbamoyl, or a benzyloxycarbonyl group (carbobenzoxy group) optionally substituted as indicated above. Suitable for alkylation are, for example, the tert.-butyl, isobutoxymethyl, benzylthiomethyl or tetrahydropyranyl radical or arylmethyl radicals optionally substituted by halogen, lower alkoxy, or nitro, such as benzyl, p-methoxybenzyl, diphenylmethyl, dimethoxybenzhydryl or, very especially, trityl, and also phenylcyclohexyl (PCH), p-methoxyphenylcyclohexyl (MPCH), thienyl(2)-cyclohexyl inter alia, cf. Ber. 101, 681, (1968). Also very advantageous is an acylaminomethyl radical of the general formula R—CO—NH—CH$_2$—in which R—CO— represents the radical of a carboxylic acid RCOOH, cf. Tetrahedron Letters 1968 (26), 3057 and German Offenlegungsschrift 2 060 969. The acyl radical R—CO— can be derived from an aliphatic, cycloaliphatic, aromatic, araliphatic or heterocyclic carboxylic acid or from a carbonic acid monoderivative, such as a carbonic acid mono-ester, or from a carbamic acid. The symbol R represents especially an optionally substituted lower alkyl radical, for example a methyl, ethyl, propyl, isopropyl, n-butyl or tert.-butyl radical, that may contain as substituents, for example, chlorine, trifluoromethyl or the nitro group. R may also represent, for example, an optionally substituted cycloalkyl radical having 3 to 8, preferably 5 or 6, ring atoms, such as the cyclopentyl or cyclohexyl radical, or an optionally substituted aromatic or araliphatic preferably monocyclic radical, especially an optionally substituted phenyl or benzyl radical, for example unsubstituted phenyl or benzyl or phenyl or benzyl substituted in the phenyl radical by lower alkyl, lower alkoxy, halogen or nitro, or a monocyclic heterocyclyl radical, for example thienyl or furyl. Of the acylaminomethyl groups the acetylaminomethyl group (acetamidomethyl group) is especially preferred. Reference has already been made hereinbefore to the special use of alkylthio groups for the protection of mercapto groups and the formation of the S-S bridge.

The protecting groups A, A', B, B' and D are preferably so chosen that they can be split off under similar conditions; particularly preferred are the groups that can be split off by acidolysis which have already been pointed out. All the protecting groups can then be split off advantageously in a single operation; it is, however, also possible to use groups of various types and to split off each one individually.

Preferably, carboxyl groups present are protected as tert.-butyl esters, ε-amino groups by the tert.-butoxycarbonyl group, the hydroxyl groups of the threonine radicals, in so far as they are protected at all, as tert.-butyl ethers, and the mercapto groups by trityl, acetamidomethyl, p-methoxybenzyl or tetrahydropyranyl groups (Thp). Except for acetamidomethyl, all these functional groups can be split off in one stage by the action of acids (acidolysis). Mercapto-protecting groups of the trityl, acetamidomethyl and tetrahydropyranyl types may also, if desired, be split off selectively while retaining the protecting groups of the tert.-butyl type by using heavy metal salts, for example mercury acetate, and hydrogen sulphide. In this manner the protected peptide is obtained with free mercapto groups. This peptide can be oxidised to form the protected disulphide of the formula IIA, characterised above, in a manner known per se, for example using iodine, diiodoethane in organic solvents or using oxygen, especially atmospheric oxygen, such as using atmospheric oxygen in liquid ammonia. It is especially advantageous to protect the mercapto groups by trityl, tetrahydropyranyl or acylaminomethyl groups and to remove these from the protected peptide using iodine, for example in methanol or acetic acid, while simultaneously forming the disulphide bridge.

The protecting groups are split off in a manner known per se; acid hydrolysis (acidolysis) is carried out, for example, by meanns of trifluoroacetic acid, hydrochloric acid or hydrofluoric acid and, in the case of acid-sensitive protecting groups, also by means of a lower aliphatic carboxylic acid, such as formic acid and/or acetic acid, in the presence of water and optionally of a polyhalogenated lower alkanol or lower alkanone, such as 1,1,1,3,3,3-hexafluoropropan-2-ol or hexafluoroacetone. The groups that can be split off by reduction, especially those that contain benzyl radicals, are preferably removed by hydrogenolysis, for example by hydrogenating with palladium catalysis. The isonicotinyloxycarbonyl group is preferably split off by zinc reduction.

Depending on the type of isolation, the end products according to the invention are obtained as bases or as acid addition salts; these may be subsequently interconverted in a manner known per se.

The formation of the above-mentioned complexes is also carried out according to known methods: complexes with sparingly soluble metal compounds, for example aluminum or zinc compounds, are preferably manufactured in an analogous manner, such as known for ACTH, for example by reacting with a soluble salt of the metal in question, for example zinc chloride or zinc sulphate, and precipitating with an alkali metal phosphate and/or hydroxide. Complexes with organic compounds, such as polyoxygelatin, carboxymethylcellulose, polyvinylpyrrolidone, polyphloretin phosphate, polyglutamic acid etc., are obtained by mixing these substances with the peptide in aqueous solution. In the same manner, it is also possible to manufacture insoluble compounds using alkali metal polyphosphates.

The starting materials of the above-characterised formulae II and IIA and, unless otherwise indicated, also the intermediates used for their synthesis, are new and some may also be advantageously used for the synthesis of other somatostatin analogues, for example those having analogous partial amino acid sequences. They, and also the processes for their manufacture, form a subject of the present invention. They are obtained according to methods known per se by condensing with one another, in any time sequence, the amino acids and smaller peptide units necessary for their synthesis, with formation of CO-NH bonds, it being possible to protect intermediately any functional groups not participating in the reaction.

In the manufacture of these starting materials, and also of all necessary intermediates, suitable protecting groups for the terminal α-amino and carboxyl groups are especially the protecting groups that are usually used in the synthesis of long-chained peptides and that can be split off readily and selectively, for example by solvolysis or reduction.

α-amino-protecting groups that should be mentioned are, for example: di- or triaryl-lower alkyl groups optionally substituted, for example, by halogen, nitro, lower alkyl or lower alkoxy, such as diphenylmethyl groups or triphenylmethyl groups, for example benzhydryl, trityl, di-(p-methoxy)-benzhydryl, or especially groups that are derived from carbonic acid and that can be split off by hydrogenolysis, such as benzyloxycarbonyl groups optionally substituted in the aromatic radical by halogen atoms, nitro groups, lower alkyl or lower alkoxy groups, for example benzyloxycarbonyl (i.e. carbobenzoxy), p-bromo- or p-chlorobenzyloxycarbonyl, p-nitrobenzyloxycarbonyl or p-methoxybenzyloxycarbonyl; also 2-(p-biphenylyl)-2-propoxycarbonyl and similar aryloxycarbonyl groups described in Swiss Patent Specification No. 509 266. It must be ensured that the α-amino-protecting group can be split off selectively while retaining the optionally present ε-amino-protecting group of the lysine radical. It is, moreover, also advantageous if, during the splitting off of the α-amino protecting group, an optionally present carboxyl- or hydroxyl-protecting group also remains undamaged.

The carboxyl-protecting groups used for this purpose are the same as those discussed above in the case of the corresponding meaning of the symbol D.

These protecting groups can be split off in known manner. For example, the benzyloxycarbonyl group can be split off by hydrogenolysis; the N-trityl group by mineral acids, such as hydrohalic acids, for example hydrofluoric acid or preferably hydrochloric acid, or by organic acids, such as formic acid, acetic acid, chloroacetic acid or trifluoroacetic acid, in aqueous or absolute trifluoroethanol as the solvent (cf. German Offenlegungsschrift DT No. 2 346 147), or by aqueous acetic acid; the tert.-butoxycarbonyl group by trifluoroacetic acid or hydrochloric acid; and the 2-(p-biphenylyl)-isopropoxycarbonyl group by aqueous acetic acid or, for example, by a mixture of glacial acetic acid, formic acid (82.8% strength) and water (7:1:2) or in accordance with the process indicated in DT No. 2 346 147.

The β-silylethyl ester groups are preferably split off by reagents yielding fluoride ions, for example fluorides or quaternary organic bases, such as tetraethylammonium fluoride. However, they can also be split off, like the conventional alkyl esters, by alkaline hydrolysis, for example by means of alkali metal hydroxides, carbonates or bicarbonates, or they can be converted by hydrazinolysis for example by means of hydrazine hydrate, into the corresponding carbazoyl groups. Acidolysis is preferably used to split off tert.-butyl esters and hydrogenolysis for benzyl esters.

The condensation of the amino acid units and/or peptide units that must be effected for the manufacture of the starting materials of the formula II is carried out in a manner known per se preferably by linking an amino acid or peptide having a protected α-amino group and an optionally activated terminal carboxyl group (=active component) to an amino acid or peptide having a free α-amino group and a free or protected, for example esterified, terminal carboxyl group (=passive component), liberating the terminal amino group in the product formed and reacting this peptide, containing a free α-amino group and an optionally protected terminal carboxyl group, with a further active component, i.e. an amino acid or peptide having an activated terminal carboxyl group and a free α-amino group, etc. The carboxyl group can be activated, for example, by converting into an acid azide, anhydride, imidazolide, isoxazolide or an activated ester, such as one of those mentioned hereinafter, or by reacting with a carbodiimide, such as N,N'-dicyclohexylcarbodiimide, optionally with the addition of N-hydroxysuccinimide, an unsubstituted or, for example, a halogen-, methyl- or methoxy-substituted 1-hydroxybenzotriazole or 4-hydroxybenzo-1,2,3-triazin-3-oxide (inter alia cf. DT Nos. 1 917 690, DT 1 937 656, DT 2 202 613), or especially with the addition of N-hydroxy-5-norbornen-2,3-dicarboximide or by reacting with N,N'-carbonyldiimidazole. The most usual coupling method is the carbodiimide method, also the azide method, the activated esters method and the anhydride method, the Merrifield method and the method using N-carboxyanhydrides or N-thiocarboxyanhydrides.

Suitable for the formation of activated esters, such as those mentioned above, are, for example, phenols and thiophenols optionally substituted by electron-attracting substituents, such as phenol, thiophenol, thiocresol, p-nitrothiophenol, 2,4,5- and 2,4,6-trichlorophenol, penta(fluoro or chloro)phenol, o- and p-nitrophenol, 2,4-dinitrophenol, p-cyanophenol, and also, for example, N-hydroxysuccinimide, N-hydroxyphthalimide and N-hydroxypiperidine.

In an especially preferred method of manufacturing the peptides of the formula II, the coupling method used is the carbodiimide method with N,N'-dicyclohexylcarbodiimide in the presence of 1-hydroxybenzotriazole. The terminal carboxyl group is protected in the form of the β-(trimethylsilyl)-ethyl ester, the α-amino group of the active component is protected by the benzyloxycarbonyl group that is split off by hydrogenolysis after each coupling step. In order to protect the ε-amino group of the lysine radicals, acylation with the tert.-butoxycarbonyl group is used and to protect the hydroxyl group of the threonine radicals, etherification with the tert.-butyl group is used. These two protecting groups may, if desired, be split off finally in one step by acid hydrolysis, for example by means of trifluoroacetic acid, hydrochloric acid or hydrofluoric acid.

The two sulphur-containing acid radicals ($Bmp^3$ and $Cys^{14}$) are preferably not introduced until the final stages of synthesis since, as is known, the presence of sulphur can impair the activity of hydrogenating catalysts and thus places in question the use of the otherwise very advantageous groups that can be split off by hydrogenolysis. The mercapto groups in the said acids are advantageously protected by the trityl groups that are especially suitable for carrying out preferred process variants.

Depending on the method used, the compounds are obtained in the form of bases or their salts. The bases can be obtained from the salts in a manner known per se and, in turn, therapeutically acceptable acid addition salts can be obtained from the bases by reacting with acids, for example with those that form the above-mentioned salts.

Owing to the close relationship between the new compounds in free form and in the form of their salts, hereinbefore and hereinafter the free compounds shall also optionally include the salts thereof and the salts shall also optionally include the free compounds.

The invention also relates to those embodiments of the process in which a compound obtainable as an intermediate at any process stage is used as the starting material and the remaining process steps are carried out, or in which a starting material is formed under the reaction conditions or is used in the form of a derivative thereof, optionally a salt.

In the process of the present invention, the starting materials used are preferably those that result in the compounds described initially as especially valuable.

The present invention also relates to pharmaceutical preparations that contain compounds of the formula I or pharmaceutically acceptable salts thereof. These pharmaceutical preparations may be used especially in the abovementioned indications if they are administered intraperitoneally, such as intravenously, intramuscularly or subcutaneously, or also intranasally. The necessary dose depends on the particular disorder to be treated, its severity and the duration of therapy. The number and quantity of the individual doses and also the administration scheme can best be determined on the basis of an individual examination of the patient concerned. The method of determining these factors is known to the man skilled in the art. As a rule, however, in the case of injection, a therapeutically active quantity of a compound of this type lies in the dosage range of approximately 0.001 to approximately 0.2 mg/kg body weight. The range of approximately 0.0015 to approximately 0.15 mg/kg body weight is preferred and administration is by intravenous infusion or subcutaneous injection. Accordingly, pharmaceutical preparations for parenteral administration in single-dose form contain per dose, depending on the type of medication, approximately 0.08 to approximately 15 mg of one of the compounds according to the invention. Apart from the active substance, they usually also contain a buffer, for example a phosphate buffer, that is to maintain the pH between 3.5 and 7, and also sodium chloride, mannitol or sorbitol for adjusting the isotonia. They may be in freeze-dried or dissolved form and solutions may advantageously contain an antibacterially active preservative, for example 0.2-0.3% of 4-hydroxybenzoic acid methyl ester or ethyl ester. If the active substance in such preparations is to be in the form of a complex having a prolonged duration of action then it may be formed directly by adding to an injection solution the complex-forming components that are prepared, for example, according to the above-mentioned methods. A suitable additive is, for example, 0.1–1.0% by weight of a zinc(II) salt (for example sulphate) in conjunction with 0.5–5.0% by weight of protamine (for example as a sulphate), calculated on the total volume of the injection solution; this preparation is in the form of a solution having a pH of 3.5 to approximately 6.5 or in the form of a suspension having a pH of approximately 7.5 to 8.0.

A preparation for intranasal administration may be an aqueous solution or gel, an oily solution or suspension, or a fat-containing salve. A preparation in the form of an aqueous solution is obtained, for example, by dissolving the active substance of the formula I, or a therapeutically acceptable acid addition salt thereof, in an aqueous buffer solution having a pH of up to 7.2 and adding a substance producing isotonia. A polymeric adhesive, for example polyvinylpyrrolidone, and/or preservative are advantageously added to the aqueous solution. The individual dose is approximately 0.08 to approximately 15 mg, preferably 0.25 to 10 mg, that are contained in approximately 0.05 ml of a solution or 0.05 g of a gel.

An oily form of medication for intranasal administration is obtained, for example, by suspending a peptide of the formula I, or a therapeutically acceptable acid addition salt thereof, in an oil, optionally with the addition of swelling agents, such as aluminium stearate, and/or interfacially active agents (surfactants), the HLB value ("hydrophilic-lipophilic balance") of which is less than 10, such as fatty acid mono-esters of polyhydric alcohols, for example glycerine monostearate, sorbitan monolaurate, sorbitan monostearate or sorbitan monooleate. A fat-containing salve is obtained, for example, by suspending the active substance according to the invention in a spreadable fat base, optionally with the addition of a surfactant having a HLB value of less than 10. An emulsion salve is obtained by triturating an aqueous solution of the peptidic active substance in a soft, spreadable fat base with the addition of a surfactant the HLB value of which is less than 10. All these intranasal forms of medication may also contain preservatives. The individual doses are approximately 0.08 to approximately 15 mg, preferably 0.25 to 10 mg, contained in approximately 0.05 to approximately 0.1 g of the base substance.

Also suitable for intranasal administration are inhalation or insufflation preparations, such as insufflation capsules that permit the active substance to be insufflated in the form of a powder with respiratory air, or aerosols or sprays that can disperse the pharmacological active substance in the form of a powder or in the form of drops of a solution or suspension. Preparations having powder-dispersing properties generally contain auxiliaries in addition to the active substance: insufflation capsules contain, for example, solid carriers, such as lactose: aerosols or spray preparations contain, for example, a liquid-propellant having a boiling point of below room temperature and, if desired, other carriers, such as liquid or solid non-ionic or anionic surfactants and/or solid diluents. Preparations in which the pharmacological active substance is in solution, contain, in addition to this, a suitable propellant and also, if necessary, an additional solvent and/or a stabiliser. Instead of the propellant, it is also possible to use compressed air that is produced when required by means of a suitable compressing and releasing device.

The invention also relates to the use of the new compounds of the formula I and therapeutically acceptable acid addition salts thereof as pharmacologically active compounds, especially in indications usual for somatostatin, preferably in the form of pharmaceutical preparations. The daily dose administered to a warm-blooded animal weighing approximately 70 kg is from approximately 0.1 to approximately 120 mg.

The invention is illustrated in the following Examples but is not limited by these. Temperatures are given in degrees Centigrade; the conventional short forms, for example those compiled in "Synthese von Peptiden" (publisher: E. Wünsch), volume XV of "Methoden der org. Chemie" (Houben-Weyl) (1974; G. Thieme, Stuttgart) are used as abbreviations, for example for denoting amino acids, peptides, protecting groups etc. The following abbreviations, in particular, are used.

Bmp—βmercaptopropionic acid
Boc—tert.-butoxycarbonyl
Bpoc—2-(p-biphenylyl)-2-propoxycarbonyl
But—tert.-butyl (as ether-forming group)
HONB—N-hydroxy-5-norbornen-endo-2,3-dicarboximide
OBut—tert.-butoxy (as ester-forming group)
ONP—p-nitrophenoxy (as ester-forming group)
OTmse—2-(trimethylsilyl)-ethoxy (as ester-forming group)
Trt—triphenylmethyl (=trityl)
Z—benzyloxycarbonyl (carbobenzoxy)
TLC—thin layer chromatography In TLC, unless otherwise indicated, silica gel is used as the adsorbent and the following systems are used as the eluant:
system
    45: sec.-butyl alcohol/3% aqueous ammonia (70:30)
    101: butanol/pyridine/acetic acid/water (38:24:8:30)
    155: pentanol/pyridine/water/butanone/acetic acid (40:28:15:11:5)
    157: chloroform/methanol/acetic acid/water (70:42:0.5:10)

EXAMPLE 1

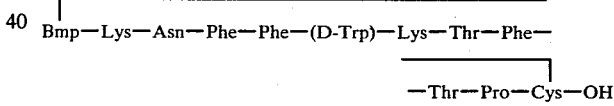

190 mg of

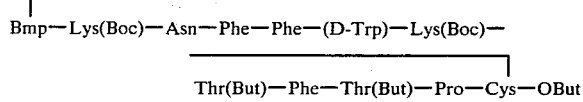

are taken up in 3.0 ml of trifluoroacetic acid/water (9:1) at 0° and are precipitated with 30 ml of ether after 30 minutes at 20°. The crude trifluoroacetate is dried in vacuo, dissolved in 5 ml of 1 N acetic acid and filtered through 15 ml of an anion exchanger in acetate form (for example AG ® 1-X8, a product of Bio-Rad Laboratories, Richmond. Calif., USA). The eluate is concentrated by evaporation in vacuo and the residue is subjected to countercurrent distribution in the system n-butanol/water/glacial acetic acid (4:5:1). After 800 distribution steps the product is in units 170-200 (K=0.26). The title compound is uniform according to thin layer chromatography.

TLC: system 157: Rf 0.15.

The starting material is manufactured in the following manner:

Stage 1.1

Z-Phe-Thr(But)-OTmse 81.65 g of dicyclohexylcarbodiimide are added to a solution of 101.82 g of Z-Phe-OH and 90.91 g of H-Thr(But)-OTmse in 660 ml of methylene chloride. After 15 hours at 20° the precipitate is filtered off, the filtrate is concentrated to half its volume and petroleum ether is added until it becomes turbid. The title compound crystallises out in the form of fine needles.

M.p. 92°–93°.$[\alpha]_D = 1°$.

Stage 1.2

H-Phe-Thr(But)-OTmse

A solution of 10 g of Z-Phe-Thr(But)-OTmse (stage 1.1) in 100 ml of methanol is hydrogenated on 1.0 g of palladium-on-carbon (10%) for one hour. The catalyst is filtered off from the reaction mixture and the solution is concentrated by evaporation, the title compound being obtained as the residue.

TLC: carbon tetrachloride/ethyl acetate (6:4): Rf 0.15.

Stage 1.3

Z-Thr(But)-Phe-Thr(But)-OTmse

A mixture of 6.12 g of Z-Thr(But)-OH, 7.62 g of H-Phe-Thr(But)-OTmse (stage 1.2) and 4.48 g of dicyclohexylcarbodiimide in 50 ml of methylene chloride is left to stand for 20 hours at 20° and filtered. The filtrate is concentrated and petroleum ether is added dropwise to the solution remaining. The precipitated product is obtained in pure form by dissolving and reprecipitating from ethyl acetate/petroleum ether.

TLC: carbon tetrachloride/ethyl acetate (6:4): Rf 0.59.

Stage 1.4

H-Thr(But)-Phe-Thr(But)-OTmse

A solution of 1.43 g of Z-Thr(But)-Phe-Thr(But)-OTmse (stage 1.3) in 14 ml of methanol is hydrogenated for 2 hours after the addition of 0.15 g of palladium-on-carbon (10%). The catalyst is filtered off and the solvent is evaporated from the filtrate, the title compound being obtained as the residue.

TLC: chloroform/methanol (95:5): Rf 0.38.

Stage 1.5

Z-(D-Trp)-Lys(Boc)-Thr(But)-Phe-Thr(But)-OTmse 0.35 g of N-hydroxybenzotriazole and 0.472 g of dicyclohexylcarbodiimide are added to a solution of 1.15 g of H-Thr(But)-Phe-Thr(But)-OTmse (stage 1.4) and 1.24 g of Z-(D-Trp)-Lys(Boc)-OH in 10 ml of acetonitrile. After 20 hours at 20° the precipitate that has separated out is filtered off, the filtrate is concentrated by evaporation and the residue is dissolved and reprecipitated from hot ethyl acetate.

TLC: cyclohexane/acetone (7:3): Rf 0.20.

Stage 1.6

H-(D-Trp)-Lys(Boc)-Thr(But)-Phe-Thr(But)-OTmse

A solution of 7.9 g of Z-(D-Trp)-Lys(Boc)-Thr(But)-Phe-Thr(But)-OTmse (stage 1.5) in 200 ml of methanol is hydrogenated for 2 hours after the addition of 1 g of palladium-on-carbon (10%). The catalyst is filtered off from the reaction solution and the solution is concentrated by evaporation, the title compound being obtained as the residue.

TLC: chloroform/methanol (8:2): Rf 0.60.

Stage 1.6A

H-Asn-Phe-Phe-OH

A solution of 20.5 g of Z-Asn-Phe-Phe-OH (see case 4-11346, stage 1.5A) in 270 ml of methanol and 30 ml of water is hydrogenated at room temperature on 2 g of palladium-on-carbon (10%) for 4 hours. After filtering off the catalyst, the filtrate is concentrated by evaporation in vacuo and the residue is used directly in the next stage.

Stage 1.6B

Z-Lys(Boc)-Asn-Phe-Phe-OH

A suspension of 15.6 g of H-Asn-Phe-Phe-OH (stage 1.6A) and 27.6 g of Z-Lys(Boc)-ONP in 200 ml of dimethylformamide, 25 ml of water and 9.2 ml of 4 N sodium hydroxide solution is stirred for 20 hours at room temperature, then neutralised by adding 36.8 ml of 1 N hydrochloric acid at 0°–5°, and 300 ml of water are added whereupon the crude product precipitates out. This is dried, stirred twice with 300 ml of ether each time and dried again. The yield is 88% of a product that is uniform according to thin layer chromatography.

TLC: butanol/acetic acid/water (3:1:1): Rf 0.82; methyl ethyl ketone/pyridine/water (65:5:20): Rf 0.53.

Stage 1.7

Z-Lys(Boc)-Asn-Phe-Phe-(D-Trp)-Lys(Boc)-Thr(But)-Phe-Thr(But)-OTmse 1.123 g of N-hydroxybenzotriazole and 1.72 g of dicyclohexylcarbodiimide are added to a solution of 5.84 g of Z-Lys(Boc)-Asn-Phe-Phe-OH (stage 1.6B) and 6.64 g of H-(D-Trp)-Lys(Boc)-Thr(But)-Phe-Thr(But)-OTmse (stage 1.6) in 30 ml of dimethylformamide. After 20 hours at 20°, the solution is filtered and the filtrate is poured into 150 ml of ice water. The precipitate is filtered off and the dried residue is dissolved and reprecipitated twice from acetonitrile/ethanol (8:2) whereupon the title compound is obtained.

TLC: chloroform/methanol/water/glacial acetic acid (88:10.5:0.5): Rf 0.44.

Stage 1.8

H-Lys(Boc)-Asn-Phe-Phe-(D-Trp)-Lys(Boc)-Thr(But)-Phe-Thr(But)-OTmse

A solution of 3.53 g of Z-Lys(Boc)-Asn-Phe-Phe-(D-Trp)-Lys(Boc)-Thr(But)-Phe-Thr(But)-OTmse (stage 1.7) in 100 ml of 90% trifluoroethanol is hydrogenated for 3 hours at room temperature after the addition of 0.4 g of palladium-on-carbon (10%); the catalyst is filtered off from the reaction solution and the solvent is evaporated off. The title compound obtained as the residue has an Rf value of 0.24 in a thin layer chromatogram on silica gel in the system chloroform/methanol/water/glacial acetic acid (88:10.5:1:0.5).

Stage 1.9

Bmp(Trt)-Lys(Boc)-Asn-Phe-Phe-(D-Trp)-Lys(Boc)-Thr(But)-Phe-Thr(But)-OTmse 0.155 g of N-hydroxybenzotriazole and 0.246 g of dicyclohexylcarbodiimide are added to 0.353 g of Bmp(Trt)-OH and 1.50 g of H-Lys(Boc)-Asn-Phe-Phe-(D-Trp)-Lys(Boc)-Thr(But)-Phe-Thr(But)-OTmse (stage 1.8) in 10 ml of dimethylformamide. After 15 hours at 20°, the solution is filtered and the filtrate is poured into 100 ml of ice water. The precipitate is filtered off and dissolved and reprecipitated from methanol.

TLC: chloroform/methanol (9:1): Rf 0.66; chloroform/methanol/water/glacial acetic acid (88:10.5:1:0.5): Rf 0.71.

Stage 1.10

Bmp(Trt)-Lys(Boc)-Asn-Phe-Phe-(D-Trp)-Lys(Boc)-Thr(But)-Phe-Thr(But)-OH 1.35 g of Bmp(Trt)-Lys(Boc)-Asn-Phe-Phe-(D-Trp)-Lys(Boc)-Thr(But)-Phe-Thr(But)-OTmse (stage 1.9) are taken up in 23 ml of a 0.15 N solution of tetraethylammonium fluoride in dimethylformamide. After 35 minutes at 30° the solution is poured into a mixture of 90 ml of water and 2.16 ml of 1 N hydrochloric acid while cooling with ice; the precipitate is filtered off, washed with a large quantity of water and dried. The title compound is obtained in the form of a white powder that is pure according to thin layer chromatography.

TLC: chloroform/isopropanol/glacial acetic acid (70:8:2): Rf 0.28; chloroform/methanol (9:1): Rf 0.20.

Stage 1.10A

Bpoc-Pro-Cys(Trt)-OBut 0.665 ml of isobutyl chlorocarbonate is added at −10° to a mixture of 1.77 g of Bpoc-Pro-OH and 0.63 ml of N-ethylmorpholine in 35 ml of tetrahydrofuran and after 15 minutes at −10° a solution of 2.135 g of H-Cys(Trt)-OBut in 25 ml of tetrahydrofuran is added dropwise; the mixture is reacted for 1 hour at −10° and for 15 hours at 20° and concentrated by evaporation. The residue is taken up in 100 ml of ethyl acetate, the solution is washed in succession with 1 N citric acid solution, 1 N sodium bicarbonate solution and water, dried over sodium sulphate and concentrated by evaporation. The product is obtained in pure form by chromatography using a column of silica gel.

TLC: toluene/acetone (7:3): Rf 0.60; ethyl acetate/petroleum ether (1:1): Rf 0.40.

Stage 1.10B

H-Pro-Cys(Trt)-OBut 3 ml of water are added dropwise to a solution of 1.13 g of Bpoc-Pro-Cys(Trt)-OBut (stage 1.10A) in 25 ml of glacial acetic acid. After one hour at 45° the mixture is concentrated by evaporation, the residue is taken up in 100 ml of ethyl acetate and the solution is washed in succession with 1 N sodium bicarbonate solution and water, dried over sodium sulphate and concentrated by evaporation. The product obtained [TLC: toluene/acetone (7:3): Rf 0.20] is used directly in the following condensation operation.

Stage 1.11

Bmp(Trt)-Lys(Boc)-Asn-Phe-Phe-(D-Trp)-Lys(Boc)-Thr(But)-Phe-Thr(But)-Pro-Cys(Trt)-OBut 123 mg of dicyclohexylcarbodiimide are added to a solution of 696 mg of Bmp(Trt)-Lys(Boc)-Asn-Phe-Phe-(D-Trp)-Lys(Boc)-Thr(But)-Phe-Thr(But)-OH (stage 1.10), 266 mg of H-Pro-Cys(Trt)-OBut (stage 1.10B) and 91 mg of N-hydroxybenzotriazole in 3 ml of dimethylformamide. After 15 hours at 20°, the solution is filtered, the filtrate is concentrated by evaporation and the residue is dissolved and reprecipitated from isopropanol. An 85% yield of the title compound is obtained in a form that is pure according to thin layer chromatography.

TLC: chloroform/methanol (9:1): Rf 0.70.

Stage 1.12

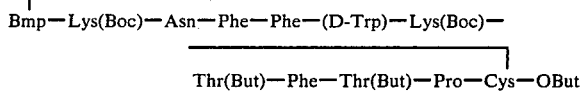

660 mg of Bmp(Trt)-Lys(Boc)-Asn-Phe-Phe-(D-Trp)-Lys(Boc)-Thr(But)-Phe-Thr(But)-Pro-Cys(Trt)-OBut (stage 1.11) are dissolved in 30 ml of dimethylformamide and added dropwise in the course of 15 minutes to a stirred solution of 711 mg of iodine in 400 ml of methanol. After a further 10 minutes a solution of 556 mg of ascorbic acid in 27 ml of water is poured in, the colourless solution is concentrated to approximately 20 ml and precipitated with 100 ml of water. The residue is dried and subjected to countercurrent distribution in the system methanol/buffer (28.6 ml of glacial acetic acid, 19.3 g of ammonium acetate, 1 liter of water)/chloroform/carbon tetrachloride (4:1:2:2). After 900 distribution steps the substance is in units 160–195 (K∼0.22).

TLC: chloroform/methanol (9:1): Rf 0.40; chloroform/isopropanol/glacial acetic acid (70:8:2): Rf 0.30.

EXAMPLE 2

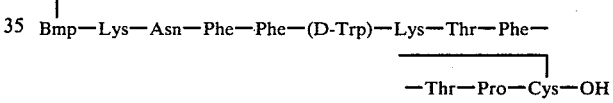

100 mg of Bmp(Trt)-Lys(Boc)-Asn-Phe-Phe-(D-Trp)-Lys(Boc)-Thr(But)-Phe-Thr(But)-Pro-Cys(Trt)-OBut (stage 1.11) are dissolved at 0° in 1.0 ml of concentrated hydrochloric acid and 50 ml of water are added after 2 minutes at 0°. After extracting three times with 50 ml of ether each time, the aqueous phase is adjusted to pH 7.4 by the addition of 12.5 ml of 1 N sodium hydroxide solution and air is passed through for 24 hours. The reaction mixture is concentrated by evaporation in vacuo, the residue is dissolved in 3 ml of acetic acid and filtered through 70 ml of an anion exchanger in acetate form (for example AG ® 1-X8, a product of Bio-Rad Laboratories, Richmond, Calif., USA). The eluate is concentrated by evaporation in vacuo and the residue is subjected to countercurrent distribution in the system n-butanol/water/glacial acetic acid (4:5:1). After 800 distribution steps the product is in units 165–195 (K∼0.23). The product is uniform according to thin layer chromatography.

TLC: system 157: Rf 0.15.

EXAMPLE 3

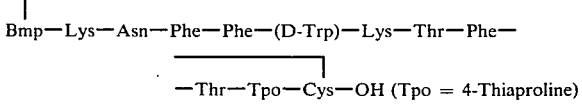

173 mg of

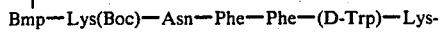
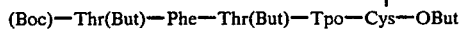

are taken up in 9.0 ml of trifluoroacetic acid/water (9:1) at 0° and precipitated with 50 ml of ether after 30 minutes at 20°. The crude trifluoroacetate is dried in vacuo and subjected to countercurrent distribution in the system n-butanol/water/glacial acetic acid (4:5:1). After 386 distribution steps the product is in units 225–280 (K=1.58). The title compound is uniform according to thin layer chromatography.

TLC: system
45: Rf 0.15
101: Rf 0.47
155: Rf 0.60

The starting material is manufactured in the following manner:

Stage 3.1

Boc-Tpo-OH (as the cyclohexylammonium salt)

4.80 g of di-tert.-butyl dicarbonate are added to a suspension of 2.66 g of 4-thiaproline and 2.12 g of sodium carbonate in a mixture of 20 ml of water and 40 ml of dioxan. After 30 minutes at 20°, the mixture is cooled to 0°–5° and adjusted to pH 2.0 with 17.5 ml of 2 N hydrochloric acid; the solution is extracted with ethyl acetate and the ethyl acetate extract is dried and concentrated by evaporation to a volume of 20 ml. 2.30 ml of cyclohexylamine are then added at 0°–5° by means of a pipette and the crystalline precipitate is filtered off and dried.

M.p.=202°–203°.
$[\alpha]_D$: $-105° \pm 1°$ (c=0.59% in CHCl$_3$).

Stage 3.2

Boc-Tpo-OTmse 2.27 g of dicyclohexylcarbodiimide are added in portions in the course of 15 minutes at −5° to a solution of 2.33 g of Boc-Tpo-OH (as the cyclohexylammonium salt, stage 3.1), 1.61 ml of pyridine and 1.59 ml of 2-trimethylsilylethanol in 30 ml of acetonitrile. After 15 hours at 5° the precipitate is filtered off, the filtrate is concentrated by evaporation, taken up in 200 ml of ethyl acetate, washed in succession with 1 N hydrochloric acid, water, 1 N sodium bicarbonate solution and water, dried over sodium sulphate and concentrated by evaporation.

TLC: chloroform/methanol (8:2): Rf 0.7.

Stage 3.3

H-Tpo-OTmse (hydrochloride)

23.4 ml of 2.1 N hydrochloric acid in ethyl acetate are added at 0° to a solution of 1.64 g of Boc-Tpo-OTmse (stage 3.2) in 4 ml of ethyl acetate. After 1¼ hours at 20°, the solution is cooled to 0° and precipitated with 200 ml of petroleum ether.

TLC: toluene/acetone (7:3): Rf 0.58.

Stage 3.3A [Bpoc-Thr(But)]$_2$O 0.62 g of dicyclohexylcarbodiimide is added to a solution of 2.48 g of Bpoc-Thr(But)-OH in 25 ml of chloroform. After 15 hours at 20°, the precipitate is filtered off and the filtrate is concentrated by evaporation.

TLC: chloroform/methanol (8:2): Rf 0.85.

Stage 3.4

Bpoc-Thr(But)-Tpo-OTmse

A solution of 0.74 g of H-Tpo-OTmse (as hydrochloride, stage 3.3), 347 µl of N-ethylmorpholine and 2.66 g of [Bpoc-Thr(But)]$_2$O (stage 3.3A) in 17 ml of dimethylformamide is left for 15 hours at 20°. The solution is concentrated by evaporation, the residue is dissolved in ethyl acetate and washed with water. After drying over sodium sulphate, the product is concentrated by evaporation and obtained in pure form by chromatography using a silica gel column.

TLC: toluene/acetone (7:3): Rf 0.73; chloroform/methanol (8:2): Rf 0.81.

Stage 3.5

Bpoc-Thr(But)-Tpo-OH

A 0.7 molar tetraethylammonium fluoride solution in dimethyl sulphoxide is added to a solution of 1.0 g of Bpoc-Thr(But)-Tpo-OTmse (stage 3.4) in 2 ml of dimethylformamide. After 1½ hours at 20° the mixture is cooled to 0° and precipitated with 100 ml of 0.01 N hydrochloric acid.

TLC: chloroform/methanol (8:2): Rf 0.32.

Stage 3.6

Bpoc-Thr(But)-Tpo-Cys(Trt)-OBut 117 mg of dicyclohexylcarbodiimide are added to a solution of 382 mg of Bpoc-Thr(But)-Tpo-OH (stage 3.5), 331 mg of H-Cys(Trt)-OBut and 141 mg of N-hydroxybenzotriazole in 7 ml of dimethylformamide. After 15 hours at 20° the precipitate is filtered off and the filtrate is concentrated by evaporation. The residue is dissolved in ethyl acetate, washed with water, dried over sodium sulphate and concentrated by evaporation. The product is purified by column chromatography using silica gel.

TLC: tetrachloromethane/ethyl acetate (6:4): Rf 0.57.

Stage 3.7

H-Thr(But)-Tpo-Cys(Trt)-OBut.hydrochloride

A solution of 307 mg of Bpoc-Thr(But)-Tpo-Cys(Trt)-OBut (stage 3.6) in 20 ml of 90% 2,2,2-trifluoroethanol is maintained at pH 1.0 at 20° for 35 minutes by slowly adding 276 µl of 1 N hydrochloric acid. The mixture is adjusted to pH 4.3 with pyridine and lyophilised from tert.-butanol.

TLC: chloroform/methanol (8:2): Rf=0.61.

Stage 3.7A

Z-Lys(Boc)-Asn-Phe-Phe-(D-Trp)-Lys(Boc)-Thr(But)-Phe-OTmse 0.81 g of HONB and 1.02 g of dicyclohexylcarbodiimide are added to a solution of 3.25 g of Z-Lys(Boc)-Asn-Phe-Phe-OH (stage 1.6B) and 3.44 g of H-(D-Trp)-Lys(Boc)-Thr(But)-Phe-OTmse in 70 ml of dimethylformamide. After 15 hours at 20° the precipitate is filtered off and the filtrate is concentrated by evaporation. The residue is triturated with a mixture of 50 ml of methanol and 150 ml of ethyl acetate, suction-filtered and dried.

TLC: chloroform/methanol (8:2): Rf 0.87.

Stage 3.7B

H-Lys(Boc)-Asn-Phe-Phe-(D-Trp)-Lys(Boc)-Thr(But)-Phe-OTmse

A solution of 5.0 g of Z-Lys(Boc)-Asn-Phe-Phe-(D-Trp)-Lys(Boc)-Thr(But)-Phe-OTmse (stage 3.7A) in 80 ml of 90% trifluoroethanol is hydrogenated for 17 hours at room temperature after the addition of 1.0 g of palladium-on-carbon (10%). The catalyst is filtered off from the reaction solution and the solvent is evaporated off. The title compound is obtained as the residue.

TLC: chloroform/methanol (8:2): Rf 0.54.

Stage 3.7C

Bmp(Trt)-Lys(Boc)-Asn-Phe-Phe-(D-Trp)-Lys(Boc)-Thr(But)-Phe-OTmse 1.23 g of dicyclohexylcarbodiimide are added to 1.19 g of Bmp(Trt)-OH and 4.58 g of H-Lys(Boc)-Asn-Phe-Phe-(D-Trp)-Lys(Boc)-Thr(But)-Phe-OTmse (stage 3.7B) and 0.61 g of HONB in 30 ml of dimethylformamide. After 15 hours at 20°, the mixture is filtered and the filtrate is poured into 250 ml of ice water. The precipitate is filtered off, dried and purified by column chromatography using silica gel.

TLC: chloroform/methanol (8:2): Rf 0.85.

Stage 3.7D

Bmp(Trt)-Lys(Boc)-Asn-Phe-Phe-(D-Trp)-Lys(Boc)-Thr(But)-Phe-OH 2.50 g of Bmp(Trt)-Lys(Boc)-Asn-Phe-Phe-(D-Trp)-Lys(Boc)-Thr(But)-Phe-OTmse (stage 3.7C) are taken up in a solution of 1.48 g of tetraethylammonium flouride in 55 ml of dimethylformamide. After 20 minutes at 30° the solution is poured into 200 ml of 0.01 N hydrochloric acid while cooling with ice and the precipitate is filtered off and dried.

TLC: chloroform/methanol (8:2): Rf 0.42.

Stage 3.8

Bmp(Trt)-Lys(Boc)-Asn-Phe-Phe-(D-Trp)-Lys(Boc)-Thr(But)-Phe-Thr(But)-Tpo-Cys(Trt)-OBut 62 mg of dicyclohexylcarbodiimide are added to a solution of 426 mg of Bmp(Trt)-Lys(Boc)-Asn-Phe-Phe-(D-Trp)-Lys(Boc)-Thr(But)-Phe-OH (stage 3.7D), 240 mg of H-Thr(But)-Tpo-Cys(Trt)-OBut.hydrochloride (stage 3.7), 41.8 µl of N-ethylmorpholine and 50 mg of HONB in 6 ml of dimethylformamide. After 15 hours at 20° the precipitate is filtered off, the filtrate is concentrated by evaporation to half its volume and precipitated with water. After suction-filtering and drying, the title compound is purified by column chromatography using silica gel.

TLC: chloroform/methanol (8:2): Rf 0.82, chloroform/methanol (95:5): Rf 0.10.

Stage 3.9

Bmp—Lys(Boc)—Asn—Phe—Phe—(D-Trp)—Lys(Boc)—
⎿——————————————————————
Thr(But)—Phe—Thr(But)—Tpo—Cys—OBut 590 mg of Bmp(Trt)-Lys(Boc)-Asn-Phe-Phe-(D-Trp)-Lys(Boc)-Thr(But)-Phe-Thr(But)-Tpo-Cys(Trt)-OBut (stage 3.8) are dissolved in a mixture of 400 ml of methanol and 10 ml of dimethylformamide, and 99.2 ml of 0.1 N iodine in methanol are added dropwise to the stirred solution. After a further 10 minutes, 13 ml of a 10% solution of ascorbic acid in water are poured in, the colourless solution is concentrated to approximately 40 ml and precipitated with 100 ml of water. The residue is dried and subjected to countercurrent distribution in the system methanol/buffer (28.6 ml of glacial acetic acid, 19.3 g of ammonium acetate, 1 liter of water)/chloroform/carbon tetrachloride (2700:675:900:1575). After 500 distribution steps the substance is in units 60–84 (K~0.15).

TLC: chloroform/methanol (8:2): Rf 0.75.

EXAMPLE 4

Bmp—Lys—Asn—Phe—Phe—(D-Trp)—Lys—Thr—Phe—Thr—
⎿——————————⎤
MeLeu—Cys—OH (MeLeu = N—Methyl-leucine)

118 mg of

Bmp—Lys(Boc)—Asn—Phe—Phe—(D-Trp)—Lys(Boc)—
⎿——————————————————————⎤
—Thr(But)—Phe—Thr(But)—Meleu—Cys—OBut are taken up in 60 ml of trifluoroacetic acid/water (9:1) at 0°, concentrated by evaporation after 30 minutes at 30° and the residue is triturated with 30 ml of ether. The crude trifluoroacetate is dried in vacuo and subjected to countercurrent distribution in the system n-butanol/water/glacial acetic acid (4:5:1). After 260 distribution steps the product is in units 35–65 (K~1.95). The title compound is uniform according to thin layer chromatography.

TLC: system 101: Rf 0.55.

The starting material is manufactured in the following manner:

Stage 4.1

Z-MeLeu-OMe 50 ml of methyl iodide are added to a solution of 25.13 g of Z-Leu-OH in 275 ml of tetrahydrofuran/dimethylformamide (10:1). 14.4 g of a dispersion of sodium hydride are added to this solution in portions within 3 hours at 20°–40° while stirring vigorously. The mixture is heated under reflux and stirred for 20 hours. The reaction mixture is concentrated by evaporation, 300 ml of ether each time are added to the residue 3 times and the whole is concentrated by evaporation. The residue is then distributed between 250 ml of water and 250 ml of ether; the ether phase is washed twice with 100 ml of water each time and the aqueous phases are then extracted with 100 ml of ether. The combined ether phases are dried over sodium sulphate, filtered and concentrated by evaporation. The product is purified by column chromatography using silica gel.

TLC: chloroform/ethyl acetate (1:1): Rf 0.67; chloroform/methanol (1:1): Rf 0.80.

Stage 4.2

Z-MeLeu-OH 23.29 g of Z-MeLeu-OMe (stage 4.1) are dissolved in 215 ml of dioxan, diluted with 72 ml of water, and 44 ml of 2 N sodium hydroxide solution are added. After stirring for 10 minutes at 20°, the solution is cooled to 0°–5° and treated dropwise with 21.8 ml of 2 N hydrochloric acid. The clear yellowish solution is concentrated by evaporation and 150 ml of ethyl acetate and 150 ml of water are added and the whole is treated dropwise in an ice bath with 21.8 ml of 2 N hydrochloric acid. The aqueous phase is separated off and then extracted again with 100 ml of ethyl acetate. The combined organic phases are washed 3 times with 100 ml of water each time, dried over sodium sulphate and concentrated by evaporation. The product is recrystallised from cyclohexane.

M.p.=74°–75°.

TLC: chloroform/ethyl acetate (1:1): Rf 0.13, chloroform/methanol (1:1): Rf 0.54.

Stage 4.3

Z-MeLeu-OTmse 2.27 g of dicyclohexylcarbodiimide are added in portions at −5° in the course of 30 minutes to a solution of 2.79 g of Z-MeLeu-OH (stage 4.2), 1.61 ml of pyridine and 1.59 ml of 2-trimethylsilylethanol in 40 ml of acetonitrile. After 15 hours at 0°–5° the precipitate formed is filtered off. The filtrate is diluted with 300 ml of ethyl acetate and washed 4 times with 25 ml each time of 2 N hydrochloric acid, 4 times with 50 ml each time of water, 4 times with 50 ml each time of 1 N sodium bicarbonate solution and 5 times with 50 ml each time of water, dried over sodium sulphate and concentrated by evaporation.

TLC: chloroform/methanol (8:2): Rf 0.80.

Stage 4.4

H-MeLeu-OTmse.hydrochloride

A solution of 3.70 g of Z-MeLeu-OTmse (stage 4.3) in 40 ml of methanol is hydrogenated for 15 minutes on 0.37 g of palladium-on-carbon (10%), the pH being maintained at 4.5 by the gradual addition of dilute hydrochloric acid. The reaction mixture is separated from the catalyst by filtration and concentrated by evaporation. The title compound is obtained in practically pure form as the residue.

TLC: chloroform/methanol (8:2): Rf 0.71.

Stage 4.5

Bpoc-Thr(But)-MeLeu-OTmse 2.43 g of [Bpoc-Thr(But)]$_2$O (stage 3.3A) are added to a solution of 0.70 g of H-MeLeu-OTmse.hydrochloride (stage 4.4) and 0.316 ml of N-ethylmorpholine in 16 ml of dimethylformamide. After 15 hours at 20° the reaction solution is concentrated by evaporation and the residue is purified by column chromatography using silica gel.

TLC: toluene/ethyl acetate (7:3): Rf 0.70.

Stage 4.6

Bpoc-Thr(But)-MeLeu-OH

A 0.70 molar solution of tetraethylammonium fluoride in dimethyl sulphoxide is added to a solution of 617 mg of Bpoc-Thr(But)-MeLeu-OTmse (stage 4.5) in 2 ml of dimethylformamide. After 1 hour at 20° the solution is precipitated with 50 ml of 0.01 N hydrochloric acid and the precipitate is filtered off and dried. TLC: toluene/ethyl acetate (7:3): Rf 0.23.

Stage 4.7

Bpoc-Thr(But)-MeLeu-Cys(Trt)-OBut 157 mg of dicyclohexylcarbodiimide are added to a solution of 344 mg of Bpoc-Thr(But)-MeLeu-OH (stage 4.6), 294 mg of H-Cys(Trt)-OBut and 125 mg of HONB in 6 ml of dimethylformamide. After 15 hours at 20° the precipitate is filtered off and the filtrate is concentrated by evaporation. The residue is purified by column chromatography using silica gel.

TLC: carbon tetrachloride/ethyl acetate (6:4): Rf 0.70.

Stage 4.8

H-Thr(But)-MeLeu-Cys(Trt)-OBut.hydrochloride

A solution of 350 mg of Bpoc-Thr(But)-MeLeu-Cys(Trt)-OBut (stage 4.7) in 20 ml of a mixture of 2,2,2-trifluoroethanol/water (9:1) is maintained for 30 minutes at pH 1.0 by the gradual addition of 0.350 ml of 1 N hydrochloric acid. The reaction mixture is adjusted to pH 4.3 with pyridine, concentrated by evaporation and lyophilised from tert.-butyl alcohol.

TLC: chloroform/methanol (8:2): Rf 0.74.

Stage 4.9

Bmp(Trt)-Lys(Boc)-Asn-Phe-Phe-(D-Trp)-Lys(Boc)-Thr(But)-Phe-Thr(But)-MeLeu-Cys(Trt)-OBut 70.6 mg of dicyclohexylcarbodiimide are added to a solution of 486 mg of Bmp(Trt)-Lys(Boc)-Asn-Phe-Phe-(D-Trp)-Lys(Boc)-Thr(But)-Phe-OH (stage 3.7D), 275 mg of H-Thr(But)-MeLeu-Cys(Trt)-OBut.hydrochloride (stage 4.8), 0.472 ml of N-ethylmorpholine and 56.2 mg of HONB in 7 ml of dimethylformamide. After 15 hours at 20° the mixture is filtered, the filtrate is concentrated by evaporation and the residue is purified by column chromatography using silica gel.

TLC: chloroform/methanol (8:2): Rf 0.82; chloroform/methanol (95:5): Rf 0.30.

Stage 4.10

```
┌─────────────────────────────────────────────────
 Bmp—Lys(Boc)—Asn—Phe—Phe—(D-Trp)—Lys(Boc)—
─────────────────────────────────────────────────┐
 —Thr(But)—Phe—Thr(But)—Meleu—Cys—OBut
```

382 mg of Bmp(Trt)-Lys(Boc)-Asn-Phe-Phe-(D-Trp)-Lys(Boc)-Thr(But)-Phe-Thr(But)-MeLeu-Cys(Trt)-OBut (stage 4.9) are dissolved in 17 ml of dimethylformamide and added dropwise in the course of 2 minutes to a stirred solution of 406 mg of iodine in 230 ml of methanol. After a further 15 minutes at 20° a solution of 318 mg of ascorbic acid in 15 ml of water is added and the colourless solution is concentrated to approximately 40 ml and precipitated with 50 ml of water. The residue is dried and subjected to countercurrent distribution in the system methanol/water/chloroform/carbon tetrachloride (2700:675:900:7575). After 380 distribution steps the substance is in units 26–45 (K∼0.08).

TLC: chloroform/methanol (8:2): Rf 0.70.

EXAMPLE 5

(A) An injection solution containing 2.0 mg of a peptide obtained according to one of Examples 1 to 4, such as

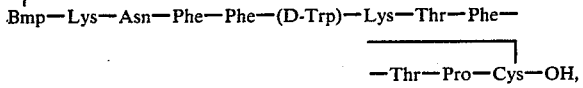

termed "active substance" in Examples 5 to 11, is obtained in the following manner:

1.0 mg of glacial acetic acid, 0.8 mg of sodium acetate, 8.0 mg of sodium chloride and 2.0 mg of active substance are dissolved in 0.7 ml of distilled water and the volume is made up to 1 ml with distilled water. The solution is heated for 20 minutes in an autoclave at 120°. After sterilisation the pH is 4.5.

(B) An injection solution containing 0.5 mg of the active substance is obtained in the following manner:

0.5 mg of active substance is dissolved in 0.7 ml of physiological sodium chloride solution and the solution is acidified with 0.1 N hydrochloric acid to pH 4.0. The volume is made up to 1 ml with distilled water and the mixture is filtered under sterile conditions.

EXAMPLE 6

(A) A gelatin-containing injection solution containing 0.1 mg of active substance is obtained in the following manner:

An aqueous solution of the active substance that has been filtered under sterile conditions is mixed, while heating, under aseptic conditions with a sterile gelatin solution, containing phenol as a preservative, so that 1.0 ml of solution has the following composition:
   active substance: 0.1 mg
   gelatin: 150.0 mg
   phenol: 4.7 mg
   distilled water to make up to: 1.0 ml.
The mixture is poured under aseptic conditions into 1.0 ml phials.

(B) An analogous injection solution containing 0.5 mg of the active substance is obtained in the same manner as indicated above by producing a mixture having the following composition:
   active substance: 0.5 mg
   gelatin: 280.0 mg
   phenol: 5.0 mg
   distilled water to make up to: 1.0 ml.
The mixture is poured under aseptic conditions into 1.0 ml phials.

EXAMPLE 7

A preparation, containing 0.5 mg of active substance, as a sterile dry substance for injection is obtained in the following manner: 0.5 mg of active substance is dissolved in 1 ml of an aqueous solution of 20 mg of mannitol. The solution is filtered under sterile conditions and poured under aseptic conditions into a 2 ml ampoule, deep-frozen and lyophilised. Before use, the lyophilisate is dissolved in distilled water. The solution is administered intramuscularly or intravenously.

EXAMPLE 8

An injection preparation containing the active substance as a polyphosphate suspension is obtained in the following manner:

(A) With 1.0 mg of active substance:

A solution of 1.0 mg of active substance and 9.0 mg of sodium chloride in 0.5 ml of distilled water is mixed with a solution of 2 mg of sodium polyphosphate "Calgon N ®" in 0.5 ml of distilled water. The suspension obtained has the following composition:
   active substance: 1.0 mg
   sodium polyphosphate (Calgon N ®): 2.0 mg
   sodium chloride: 9.0 mg
   distilled water to make up to: 1.0 ml.
The suspension has a pH of 6.9. It is suitable for intramuscular administration.

(B) With 0.5 mg of active substance:

In the same manner as indicated above, a suspension having the folliwing composition is produced:
   active substance: 0.5 mg
   sodium polyphosphate (Calgon 322 ®): 1.0 mg
   sodium chloride: 9.0 mg
   distilled water to make up to: 1.0 ml.
The pH of the suspension is 5.9.

EXAMPLE 9

Injection preparation containing 0.3 mg of active substance in the form of an oily aluminium stearate gel A 2% aluminium stearate gel is prepared in the usual manner by suspending 1.0 g of aluminium monostearate in 49.0 g of peanut oil and then heating at 130° for 10 minutes. 15.0 mg of active substance are suspended with 0.3 g of the above aluminium stearate gel, homogenised and diluted with the remaining quantity of the aluminium stearate gel. The gel so obtained has the following composition:
   active substance: 0.3 mg
   aluminium monostearate: 20.0 mg
   peanut oil to make up to: 1.0 ml.
The oily aluminium stearate gel suspension is suitable for intramuscular administration.

EXAMPLE 10

Injection preparation containing 0.5 mg of active substance as a depot suspension with dextran sulphate 0.36 mg of acetic acid, 1.9 mg of sodium acetate trihydrate, 0.8 mg of sodium chloride and 0.5 mg of active substance are dissolved in 0.4 ml of distilled water and the volume is made up to 0.5 ml with distilled water. 0.5 ml of a 0.1% solution of dextran sulphate (molecular weight 500,000) is added to this solution while stirring, a homogeneous precipitate being formed. The suspension obtained has the following composition:
   active substance: 0.50 mg
   dextran sulphate MW 500,000: 0.50 mg
   acetic acid 100%: 0.36 mg
   sodium acetate trihydrate: 1.90 mg
   sodium chloride: 0.80 mg
   distilled water to make up to: 1.00 ml.
The aqueous suspension is suitable for intramuscular and subcutaneous injection.

EXAMPLE 11

Nasal spray 30 mg of finely ground active substance is suspended in a mixture of 75 mg of benzyl alcohol and 1.395 g of Miglyol 812. This suspension is placed in aluminium monobloc containers (content 10 ml) that are then closed with a metering valve and 6.0 g of freon 12/114 (40:60) are added under nitrogen pressure. The aluminium container having a total charge of 7.5 g contains 100 individual doses each containing 0.3 mg of active substance. The spray container is so adjusted by means of the valve that a single dose is sprayed by pressing once. Nasal sprays that contain, instead of the Miglyol, the same quantity of isopropyl myristate or isopropyl palmitate or "Labrafac WL 1219" (a mixture of glycerol and polyoxyethylene glycol esters of fatty acids having 8 and 10 carbon atoms) are manufactured in the same manner.

We claim:

1. A somatostatin-analogous peptide of the general formula

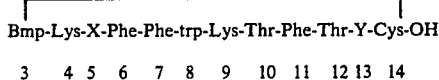

$$\text{Bmp-Lys-X-Phe-Phe-trp-Lys-Thr-Phe-Thr-Y-Cys-OH}$$
$$\phantom{\text{Bmp-Lys-}}3\phantom{\text{-}}4\phantom{\text{-}}5\phantom{\text{-}}6\phantom{\text{-}}7\phantom{\text{-}}8\phantom{\text{-}}9\phantom{\text{-}}10\phantom{\text{-}}11\phantom{\text{-}}12\phantom{\text{-}}13\phantom{\text{-}}14$$

in which

Bmp represents the desaminocysteine radical,

X represents Asn or His, trp represents D-Trp that may be substituted in the benzene ring by a halogen atom, and Y represents the radical of an alpha-(lower alkyl)amino-(lower alkyl)carboxylic acid having a minimum of 4 and a maximum of 8 carbon atoms or said radical in which the two lower alkyl radicals are connected to one another with a single C—C bond, an oxygen atom or a sulphur (II) atom, and a corresponding peptide amide, and also acid addition salts of said compounds.

2. A pharmaceutical preparation for treating acromegalia, diabetes or inhibiting blood loss in the gastro-intestinal tract, containing an effective amount of a compound of claim 1.

3. A method for treating acromegalia, diabetes or inhibiting blood loss in the gastro-intestinal tract in a warm-blooded animal including man, which comprises administering to said animal an effective amount of a compound of claim 1, together with at least one pharmaceutically acceptable auxiliary or carrier material.

4. A method of claim 3, wherein the compound is administered for the treatment of diabetes.

5. A compound of claim 1 in which
X represents Asn,
trp represents D-trp or 5-fluoro-D-Trp and
Y represents Pro, the radical of 4-thiaproline or N-methyl-Leu.

6. [Desamino-Cys$^3$-D-Trp$^8$-Pro$^{13}$]-somatostatin(3–14).

7. [Desamino-Cys$^3$-(5-fluoro-D-Trp)$^8$-Pro$^{13}$]-samatostatin(3–14).

8. [Desamino-Cys$^3$-D-Trp$^8$-Tpo$^{13}$]-samatostatin(3–14).

9. [Desamino-Cys$^3$-D-Trp$^8$-MeLeu$^{13}$]-samatostatin(3–14).

10. Pharmaceutically acceptable acid addition salts of compounds according to claim 1.

* * * * *